US009511165B2

(12) United States Patent
Vlad et al.

(10) Patent No.: US 9,511,165 B2
(45) Date of Patent: Dec. 6, 2016

(54) WATER-BASED AIR FRESHENER COMPOSITIONS, SYSTEMS, AND METHODS OF USE THEREOF

(75) Inventors: Florin-Joseph Vlad, Annandale, NJ (US); Stuart A. Zlotnik, Montville, NJ (US); Natalie Hinden-Kuhles, Somerville, NJ (US)

(73) Assignee: Agilex Flavor & Fragrances, Piscataway, NJ (US)

( * ) Notice: Subject to any disclaimer, the term of this patent is extended or adjusted under 35 U.S.C. 154(b) by 0 days.

(21) Appl. No.: 13/280,340

(22) Filed: Oct. 24, 2011

(65) Prior Publication Data

US 2012/0097754 A1   Apr. 26, 2012

Related U.S. Application Data

(60) Provisional application No. 61/405,957, filed on Oct. 22, 2010.

(51) Int. Cl.
*A61L 9/04* (2006.01)
*A61L 9/01* (2006.01)
*A61L 9/14* (2006.01)

(52) U.S. Cl.
CPC ... *A61L 9/01* (2013.01); *A61L 9/14* (2013.01)

(58) Field of Classification Search
CPC ........................................ A61L 9/01
USPC ............................................ 512/1
See application file for complete search history.

(56) References Cited

U.S. PATENT DOCUMENTS

| 4,663,081 | A | * | 5/1987 | Grimshaw et al. ............... 512/3 |
| 4,983,578 | A |   | 1/1991 | Cashman et al. |
| 5,047,234 | A |   | 9/1991 | Dickerson et al. |
| 5,585,343 | A | * | 12/1996 | McGee et al. ............... 512/1 |
| 6,180,595 | B1 |  | 1/2001 | Van Walsum et al. |
| 2008/0023569 | A1 | | 1/2008 | O'Leary et al. |
| 2011/0095097 | A1 | | 4/2011 | Herd et al. |

OTHER PUBLICATIONS

Butyl Carbitol Product Information from Dow Corning. Oct. 3, 2012. Obtained at http://msdssearch.dow.com/PublishedLiteratureDOWCOM/dh_08ac/0901b803808aca8a.pdf?filepath=oxysolyents/pdfs/noreg/110-00624.pdf&fromPage=GetDoc.*
International Search Report mailed Jun. 4, 2012, in corresponding PCT patent application No. PCT/US2011/057554.
Examination report in European Patent Application No. 11 835 295.4-1370, enclosing a copy of result of consultation (May 17, 2016).
Applicant Letter to European Patent Office (May 27, 2016).
Amended claims (clean) enclosed with Applicant Letter to European Patent Office (May 27, 2016).
Amended claims (tracked) enclosed with Applicant Letter to European Patent Office (May 27, 2016).
Amended description (clean) enclosed with Applicant Letter to European Patent Office (May 27, 2016).
Amended description (tracked) enclosed with Applicant Letter to European Patent Office (May 27, 2016).
Communication under Rule 71(3) EPC of Intention to Grant—European Patent Application No. 11835295,4 dated Aug. 16, 2016 (39 pages).

* cited by examiner

*Primary Examiner* — Ling Choi
*Assistant Examiner* — Lanee Reuther
(74) *Attorney, Agent, or Firm* — Finnegan, Henderson, Farabow, Garrett & Dunner, LLP

(57) ABSTRACT

Air freshener compositions, devices, and methods are disclosed.

24 Claims, No Drawings

WATER-BASED AIR FRESHENER COMPOSITIONS, SYSTEMS, AND METHODS OF USE THEREOF

RELATED APPLICATIONS

This application claims the benefit of and priority to U.S. Provisional Patent Application Ser. No. 61/405,957, filed Oct. 22, 2010, the contents of which are incorporated herein by reference.

TECHNICAL FIELD

The present invention relates to air freshener devices comprising clear, stable, aqueous rich liquid compositions with customable level of fragrance ingredients, herein named perfume, and improved perfume release performance, regardless the physical characteristics of fragrance ingredients such as ClogP values.

Also, the invention provides air freshener devices for use with such compositions; the devices can include, e.g., an emanating surface, which allows the diffusion of perfume, or an actuator nozzle, which allows the spraying of perfume.

BACKGROUND OF THE INVENTION

Air fresheners are conventionally used to provide a desired fragrance to ambient air, or to mask, neutralize or counteract undesirable odors in the air, or to achieve a combination of these functions.

Many liquid air fresheners are commercially available in different formats such as reed or wick diffusers, electrical plug-in devices, aerosols, or sprays (see, e.g., U.S. Pat. No. 6,180,595; U.S. Patent Publication No. 2008/0023569, and U.S. Patent Publication No. 2011/0095097. The perfume composition of the air freshener may be a fragrance concentrate, a true solution, or a colloidal solution such as a microemulsion. However, conventional liquid air fresheners often suffer from certain disadvantages and limitations. For example, air freshener performance may be unsatisfactory due to limited or even unacceptable fragrance performance, product longevity, esthetical appearance, or temperature product stability over time. Certain air fresheners include high levels of volatile organic compound (VOC) solvents, which are disfavored due to environmental and safety concern, and may raise regulatory concerns.

Also, many conventional air freshener formulations, including aqueous-based formulations, impose restrictions in fragrance creativity and limitations on the level of fragrance that can be employed due to fragrance solubility or solubilization issues. For example, perfumed liquid air fresheners containing high level of water often require large amounts of solubilizers, such as surfactants, in order to achieve the desired clarity and stability of the final products. Such products may contain excess amounts of solubilizers with respect to the perfume; sometimes the weight ratio of surfactant to perfume is at least 1.5:1 or even higher, which may have unsatisfactory impact on fragrance performance over time, such as fragrance release and fragrance perception (intensity, character, and the like). The use of high levels of solubilizers can lead to unacceptable product performance, such as limited performance over time due to suppressed or poor fragrance release through delivery device such as wicks or reeds as a result of the solubilizer clogging the capillary channels in the diffuser. Similarly, high levels of solubilizers can result in clogging of the actuator in nozzle sprays.

Therefore, there is a need for improved air freshener formulations to address these and other problems.

SUMMARY OF THE INVENTION

The present invention provides stable, clear-transparent, perfumed aqueous formulations (such as microemulsions) with low level of VOCs (e.g., below the 18% w/w VOC limit imposed by CARB (California Air Resources Board) for air fresheners), which displays excellent fragrance performance during usage, such as fragrance longevity, fragrance intensity and character, and excellent shelf stability. The fragrance can be released into ambient air through dispersing devices such as wicks, reeds, or any natural or synthetic porous diffusers, as well as actuators associated with nozzle sprays. The formulations of the present invention impose fewer restrictions in fragrance creativity to be employed in water-rich products designed for liquid air fresheners. The compositions of the present invention advantageously can offer low-cost formulations for products that provide fragrance for at least 14 days, e.g., up to 90 days, while the product's clarity is maintained until the end of usage (e.g., when the reservoir is completely emptied of product).

In one aspect, the invention provides a stable, clear-transparent, low viscosity liquid air freshener composition comprising: (a) 0.1% to 60% (e.g., 0.5% to 60% or 0.1% to 40%) by weight of an oil phase comprising at least one fragrance ingredient (b) a low VOC or completely non-VOC fragrance vehicle comprising at least one mono-, di-, or polyglycol ethers; (c) a low level of amphiphilic solubilizing agent, such as surfactants; and (d) at least 10%, or at least 30% by weight of water, wherein the weight percentages are expressed as weight/weight relative to the total weight of liquid composition.

In another aspect, the invention provides an air freshener system, comprising (i) a container; (ii) stable, clear-transparent, low viscosity liquid air freshener composition comprising: (a) 0.1% to 60% (e.g., 0.5% to 60% or 0.1% to 40%) by weight of an oil phase comprising at least one fragrance ingredient (b) a low VOC or completely non-VOC fragrance vehicle comprising at least one mono-, di-, or polyglycol ethers; (c) a low level of amphiphilic solubilizing agent, such as surfactants; and (d) at least 10%, or at least 30% by weight of water, wherein the weight percentages are expressed as weight/weight relative to the total weight of liquid composition; and (iii) a diffuser, e.g., one or wicks, reeds, or any other material that allows the diffusion of liquid air freshener composition into ambient air, e.g., a diffuser that linearly releases the liquid composition into surrounding air for a customizable length of time; or (iv) a nozzle with an actuator for spraying the composition into surrounding air.

In a further aspect, the invention provides a method of providing a fragrance to ambient air, the method comprising diffusing or spraying a composition of the invention as described herein into the ambient air.

In one aspect, the invention provides a liquid air freshener composition, the composition comprising:

(a) 0.1% to 60% by weight of an oil phase comprising a fragrance;

(b) at least 10% by weight of water;

(c) a fragrance vehicle comprising at least one mono-, di-, or polyglycol ether; and (d) an amphiphilic solubilizing agent.

In certain embodiments, the composition comprises:

(a) 0.5% to 60% by weight of an oil phase comprising a fragrance;

(b) at least 10% by weight of water;
(c) a fragrance vehicle comprising at least one mono-, di-, or polyglycol ether; and
(d) an amphiphilic solubilizing agent.

In certain embodiments, the composition comprises:
(a) 0.1 to 40% by weight of an oil phase comprising a fragrance;
(b) an amphiphilic oil solubilizing agent comprising one or more ionic, non-ionic, cationic or amphoteric surfactants, or a mixture thereof;
(c) at least 30% by weight of water; and
(d) a low VOC fragrance vehicle comprising at least one linear, branched, cyclic, or aromatic mono-, di- or polyglycol-ether.

In certain embodiments, the composition is a clear isotropic composition. In certain embodiments, the composition is a microemulsion or nanoemulsion. In certain embodiments, the composition is a solution. In certain embodiments, the solution is a micellar solution.

In certain embodiments, the fragrance component comprises one or more fragrance components selected from the group consisting of ketones, aldehydes, esters, alcohols, ethers, terpenes, natural essential oils, and synthetic musk. In certain embodiments, the fragrance component is selected from the group consisting of aliphatic hydrocarbons, terpene hydrocarbons, aromatic hydrocarbons, aliphatic alcohols, terpene alcohols, aromatic alcohols, aliphatic ethers, aromatic ethers, aliphatic oxides, terpene oxides, aliphatic aldehydes, terpene aldehydes, hydrogenated aromatic aldehydes, thioaldehydes, aromatic aldehydes, aliphatic ketones, terpene ketones, hydrogenated aromatic ketones, cyclic ketones, aromatic ketones, acetals, ketals, phenols, phenol ethers, fatty acids, hydrogenated aromatic carboxylic acids, aromatic carboxylic acids, acid amides, aliphatic lactones, macrocyclic lactones, terpene lactones, hydrogenated aromatic lactones, aromatic lactones, aliphatic esters, furan carboxylic esters, alicyclic carboxylic esters, cyclohexylcarboxylic esters, terpene carboxylic esters, aromatic carboxylic esters, nitromusks, nitriles, amines, pyridines, quinolines, pyrroles, and indoles.

In certain embodiments, the amphiphilic solubilizing agent comprises one or more surfactants or hydrotropic molecules, or a combination thereof. In certain embodiments, the amphiphilic solubilizing agent comprises one or more ionic, non-ionic, anionic, cationic or amphoteric surfactants. In certain embodiments, the amphiphilic solubilizing agent comprises one or more anionic surfactants. In certain embodiments, the one or more anionic surfactants comprises a sulfosuccinate ester.

In certain embodiments, the fragrance vehicle comprises 2-(2-butoxy-ethoxy)ethanol or (2-methoxy-methylethoxy)propanol.

In certain embodiments, the air freshener further comprises one or more antioxidants, UV stabilizers, buffer agents, pH controlling mixtures, malodor control agents, and antibacterial agents.

In certain embodiments, the air freshener composition has 18% or less volatile organic compounds as defined by CARB.

In certain embodiments, the fragrance vehicle is a low VOC fragrance vehicle. In certain embodiments, the low VOC fragrance vehicle is substantially a non-VOC fragrance vehicle.

In certain embodiments, the fragrance vehicle comprises a material selected from the group consisting of dihydric alcohol alkyl ethers; dihydric alcohol alkyl ethers; dihydric alcohol ether esters; glycerol monoalkyl ethers; POP butyl ether, POP-POE butyl ether, tripolyoxypropylene glycerol ether, POP glycerol ether, POP glycerol ether phosphate, and POP.POE pentaerythritol ether; or a mixture thereof. In certain embodiments, the dihydric alcohol alkyl ether is selected from the group consisting of ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene, glycol diethyl ether, and ethylene glycol dibutyl ether. In certain embodiments, the dihydric alcohol alkyl ether is selected from the group consisting of diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether.

In certain embodiments, the dihydric alcohol ether ester is selected from the group consisting of ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate. In certain embodiments, the glycerol monoalkyl ether is selected from the group consisting of chimyl alcohol, selachyl alcohol, and butyl alcohol.

In certain embodiments, the composition comprises between 10% to 30% fragrance vehicle.

In certain embodiments, the liquid composition comprises a solubilizing agent at a weight ratio between 0.1:1 to 1:1 relative to the weight of the oil phase.

In certain embodiments, the anionic surfactant is selected from the group consisting of sodium laurate, and sodium palmitate; higher alkyl sulfuric ester salts, such as sodium laurylsulfate and potassium laurylsulfate; alkyl ether sulfuric ester salts, such as triethanolamine POE laurylsulfate and sodium POE laurylsulfate; N-acylsarcosinic acids, such as sodium lauroylsarconinate, higher fatty acid amidosulfonates, such as sodium N-myristoyl-N-methyltaurine, sodium palm oil fatty acid methyltauride, and sodium laurylmethyltauride; phosphoric ester salts, such as sodium POE oleyl ether phosphate and POE stearyl ether phosphate; sulfosuccinates, such as sodium di-2-ethylhexylsulfosuccinate, and sodium lauryl polypropylene glycol sulfosuccinate; alkylbenzenesulfonates, such as sodium linear dodecylbenzenesulfonate, triethanolamine dodecylbenzenesulfonate, and linear dodecylbenzenesulfonic acid; N-acylglutamates, such as monosodium N-lauroylglutamate, disodium N-stearoylglutamate, monosodium N-myristoyl-L-glutamate; higher fatty acid ester sulfuric ester salts, such as sodium hydrogenated coconut oil fatty acid glycerol sulfate; sulfated oils, such as Turkey red oil; POE alkyl ether carboxylic acids, POE alkyl allyl, ether carboxylates, α-olefinsulfonates, higher fatty acid ester sulfonates, secondary alcohol sulfuric ester salts, higher fatty acid alkylolamide sulfuric ester salts, sodium lauroyl monoethanolamide succinate, ditriethanolamine N-palmitoylaspartate, and sodium casein In certain embodiments, the cationic surfactant is selected from the group consisting of stearyltrimethylammonium chloride and lauryltrimethylammonium chloride; dialkyldimethylammonium salts, such as distearyldimethylammonium chloride, alkylpyridinium salts, such as poly-N,N'-dimethyl-3,5-methylenepiperidinium chloride; alkyl quaternary ammonium salts, alkyldimethylbenzylammonium salts, alkylisoquinolinium salts, dialkylmorpholinium salts, POE alkylamines, alkylamine salts, polyamine fatty acid derivatives, amyl alcohol fatty acid derivatives, benzalkonium chloride, and benzethonium chloride.

In certain embodiments, the amphoteric surfactant is selected from the group consisting of sodium 2-undecyl-N,N,N-(hydroxyethylcarboxymethyl)-2-imidazoline and disodium 2-cocoyl-2-imidazolinium hydroxide-1-carboxyethyloxy; 2-heptadecyl-N-carboxymethyl-N-hydroxyethylimidazolinium betaine, alkyl betaines, amide betaines, and sulfobetaines.

In certain embodiments, the composition is an oil-in-water microemulsion, an emulsion or a nanoemulsion.

In certain embodiments, the composition is a solution. In certain embodiments, the solution is a micellar solution.

In another aspect, the invention provides an air freshener system, comprising:
(i) a container;
(ii) an air freshener composition of the invention as described herein; and
(iii) a diffuser for diffusing the liquid composition into surrounding air.

In certain embodiments, the diffuser is a natural or synthetic porous material that allows the diffusion of the composition. In certain embodiments, the diffuser comprises one or more wicks, reeds, or natural or synthetic porous diffusers. In certain embodiments, the diffuser is a wick or a reed diffuser.

In certain embodiments, the air freshener system further comprises removable means for preventing diffusion of the liquid composition into surrounding air.

In certain embodiments, the air freshener system releases fragrance for about 6 to about 14 weeks after opening. In certain embodiments, the air freshener system releases fragrance for at least 2 weeks after opening.

In another aspect, the invention provides an air freshener system, comprising:
(i) a container;
(ii) an air freshener composition of the invention as described herein; and
(iii) means for carrying the liquid composition from the container to an emanating nozzle for spraying the said composition; and
(iv) an actuator device for controlling the spraying of the said liquid composition from the container into the surrounding air environment.

In another aspect, the invention provides a method of providing a fragrance to ambient air, the method comprising diffusing a liquid air freshener composition with a device of the invention as described herein, into the ambient air.

In another aspect, the invention provides a method for perfuming, refreshing, disinfecting or cleaning ambient air, the method comprising diffusing a liquid air freshener composition of the invention as described herein into the ambient air.

In certain embodiments, a device of the invention is used to diffuse the liquid air freshener composition of the invention into the ambient air In still another aspect, the invention provides a consumer article comprising a composition of the invention as described herein that can be diffused or sprayed in rooms and open spaces, closets, cupboards and other closed environments.

Other aspects, embodiments, features and advantages of the present invention will be apparent from the description herein.

DETAILED DESCRIPTION OF THE INVENTION

The invention provides a stable, clear-transparent, air freshener composition and device to perfume, refresh or to mask, neutralize or counteract undesirable odours in the air and the surroundings thereof, or to achieve a combination of the mentioned functions.

In one aspect, the compositions of the invention are stable, clear-translucent, low viscosity liquid fragrance compositions which, in use, may be contained in a vessel or container means to carry the liquid composition from the containing vessel either to an emanating surface from which the composition can diffuse into the surroundings or can be released by spraying through a nozzle. The compositions of the invention include
(a) 0.1% to 60% by weight of an oil phase comprising a fragrance;
(b) at least 10% by weight of water;
(c) a fragrance vehicle comprising at least one mono-, di-, or polyglycol ether; and
(d) an amphiphilic solubilizing agent.

In certain embodiments, the liquid composition comprises: 0.1 to 40% w/w oil-phase (also referred to herein as "perfume"); a low VOC or completely non-VOC fragrance vehicle, which contains one or more mono-, di- or polyglycol ethers, such as 2-(2-butoxy-ethoxy)ethanol or (2-methoxy-methoxyethoxy) propanol or established mixtures thereof;
(i) an amphiphilic solubilizing agent or agents, such as surfactants;
(ii) at least 30% w/w water;
wherein the weight percentages being relative to the total weight of the liquid composition.

According to one embodiment of the invention the fragrance vehicle is present in the liquid composition in a concentration between 10 to 30% w/w, relative to the total weight of liquid composition, and the weight ratio of amphiphilic solubilizing agent to oil phase (perfume) is less than or equal to 1, e.g., 0.1:1 to about 1:1.

In certain embodiments, the composition is a stable, clear-transparent oil-in-water microemulsion, emulsion or nanoemulsion. As used herein, the term "clear-transparent" refers to a composition that transmits light without significant visible scattering or distortion when the light scattered is measured at an angle of 90°. In certain embodiments, the composition has clarity or transparency of between 0 and 100 NTU (Nephelometric Turbidity Units), preferably between 0 and 50 NTU, when measured with light wavelength between 400 and 600 nm in a 2.5 cm cell at room temperature (25° C.). In certain embodiments, the composition is a solution. In certain embodiments, the solution is a micellar solution.

The compositions of the present invention can be prepared according to any suitable method, some of which are known in the art. A common method includes dissolving the solubilizing agent and the low VOC fragrance vehicle into the water to form a clear-translucent micellar solution. To the resulting micellar solution is added, under normal stirring, the perfume (oil phase) when a clear-translucent oil-in-water microemulsion forms. Typically, a clear-translucent product is obtained immediately.

In another aspect, the invention relates to a method for preparing a liquid air freshener composition of the invention. The method comprises the steps of (a) combining a solubilizing agent and a low VOC fragrance vehicle (as described herein) with water to form a clear-translucent micellar solution, and (b) to the resulting micellar solution, adding (with optional stirring) the perfume (oil phase) to obtain a liquid air freshener composition of the invention (e.g., a clear-translucent oil-in-water microemulsion).

The invention also provides a composition liquid air freshener composition prepared by combining (a) 0.1% to 60% by weight of an oil phase comprising a fragrance;

(b) at least 10% by weight of water;

(c) a fragrance vehicle comprising at least one mono-, di-, or polyglycol ether; and (d) an amphiphilic solubilizing agent.

The liquid compositions of the invention also display excellent stability, e.g., clarity, no phase separation, within a reasonable period of time. In certain embodiments, a composition of the invention is stable for at least 15 days, or at least 30 days at room temperature, or at a temperature between 10° C. and 50° C. In certain embodiments, a composition of the invention is stable for at least about 6 months at a temperature between 5° C. and 45° C. However, the range of temperatures and stability of the composition depend at least in part on the amount and nature of the perfume oil, amount and composition of fragrance vehicle, and the amount and type of the solubilizing agent. Other optional ingredients, whether oil-soluble or water-soluble, can influence the long term product stability. In general, formulations are selected to provide acceptable stability as described herein.

The term perfume or "fragranced ingredients" refer to fragrance components commonly employed in the art in an appropriate combination, such as ketones, aldehydes, esters, alcohols, ethers, terpenes, natural essential oils, and synthetic musk. In other words, the fragranced ingredients that can be used in the invention are not particularly limited, and include those usually used in various fragranced products known in the art, such as preparations for external application to skin (e.g., cosmetics and pharmaceuticals), detergents and cleansers for washing skin, hair, clothes, and hard surfaces, bleachers, and softeners. Suitable fragranced ingredients include synthetic and natural materials (e.g., of animal or plant origin). Examples of fragranced ingredients include hydrocarbons, such as aliphatic hydrocarbons, terpene hydrocarbons, and aromatic hydrocarbons; alcohols, such as aliphatic alcohols, terpene alcohols, and aromatic alcohols; ethers, such as aliphatic ethers and aromatic ethers; oxides, such as aliphatic oxides and terpene oxides, aldehydes, such as aliphatic aldehydes, terpene aldehydes, hydrogenated aromatic aldehydes, thioaldehydes, and aromatic aldehydes; ketones, such as aliphatic ketones, terpene ketones, hydrogenated aromatic ketones, cyclic ketones, and aromatic ketones; acetals, ketals, phenols, phenol ethers; acids, such as fatty acids, hydrogenated aromatic carboxylic acids, and aromatic carboxylic acids; acid amides; lactones, such as aliphatic lactones, macrocyclic lactones, terpene lactones, hydrogenated aromatic lactones' and aromatic lactones; esters, such as aliphatic esters, furan carboxylic esters, alicyclic carboxylic esters, cyclohexylcarboxylic esters, terpene carboxylic esters, and aromatic carboxylic esters; and nitrogen-containing compounds, such as nitromusks, nitriles, amines, pyridines, quinolines, pyrrole, and indole. Typical fragranced ingredients useful in the compositions and devices of the present invention include: $C_6$-$C_{12}$ aldehydes, anisaldehyde, acetal R, acetophenone, acetylcedrene, adoxal, allylamyl glycolate, allyl cyclohexanepropionate, α-damascene, β-damascone, δ-damascone, ambrettolide, ambroxan, amylcinnamic aldehyde, amylcinnamic aldehyde dimethylacetal, amyl valerianate, amyl salicylate, isoamyl acetate, isoamyl salicylate, aurantiol, acetyl eugenol, bacdanol, benzyl acetate, benzyl alcohol, benzyl salicylate, bergamyl acetate, bornyl acetate, butyl butyrate, p-t-butylcyclohexanol, p-t-butylcyclohexyl acetate, o-t-butylcyclohexanol, benzaldehyde, benzyl formate, caryophyllene, cashmerane, carvone, cedramber, cedryl acetate, cedrol, celestolide, cinnamic alcohol, cinnamic aldehyde, cis-jasmone, citral, citral dimethyl acetal, citrasal, citronellal, citronellol, citronellyl acetate, citronellyl formate, citronellyl nitrile, cyclaset, cyclamen aldehyde, cyclaprop, caron, coumarin, cinnamyl acetate, $\gamma$-$C_6$-$C_{13}$ lactone, dimethylbenzylcarbinol, dihydrojasmon, dihydrolinalool, dihydromyrcenol, dimetol, dimyrcetol, diphenyl oxide, ethyl vanillin, eugenol, fruitate, fenchyl alcohol, phenylethyl phenylacetate, galaxolide, $\gamma$-$C_6$-$C_{13}$ lactone, geraniol, geranyl acetate, geranyl formate, geranyl nitrile, hedion, helional, heliotropin, cis-3-hexanol, cis-3-hexenyl acetate, cis-3-hexenyl salicylate, hexylcinnamic aldehyde, hexyl salicylate, hyacinth dimethyl acetal, hydrotropic alcohol, hydroxycitronellal, indole, ionone, isobornyl acetate, isocyclocitral, Iso E Super, isoeugenol, isononyl acetate, isobutylquinoline, jasmal, jamolactone, jasmopirane, corvone, ligustoral, lilial, lime oxide, limonene, linalool, linalool oxide, linalyl acetate, lyral, manzanate, myol, menthanyl acetate, menthonate, methyl anthranilate, methyl eugenol, menthol, α-methylionone, β-methylionone, γ-methylionone, methyl isoeugenol, methyl lavender ketone, methyl salicylate, muguet aldehyde, mugol, musk TM-II, musk 781, musk C14, musk T, musk ketone, musk tibetene, musk moskene, myrac aldehyde, methyl phenyl acetate, nerol, neryl acetate, nopyl acetate, nopyl alcohol, neobergamate, oak moss No. 1, orivone, oxyphenylon, p-cresyl methyl ether, pentalide, phenylethyl alcohol, phenylethyl acetate, phenylacetaldehyde, dimethyl acetal, α-pinene, rubafuran, rosephenone, rose oxide, Sandalore, Sandela, Santalex, Santalinol, styralyl acetate, styralyl propionate, terpineol, terpinyl acetate, tetrahydrolinalool, tetrahydrolinalyl acetate, tetrahydrogeraniol, tetrahydrogeranyl acetate, tonalide, traseolide, tripral, thymol, vanillin, verdox, yara yara, anis oil, bay oil, bois de-rose oil, cananga oil, cardamom oil, cassia oil, cedarwood oil, orange oil, mandarin oil, tangerine oil, basil oil, nutmeg oil, citronella oil, clove oil, coriander oil, elemi oil, eucaryptus oil, fennel oil, galbanum oil, geranium oil, hiba oil, hinoki oil, jasmine oil, lavandin oil, lavender oil, lemon oil, lemongrass oil, lime oil, neroli oil, oak moss oil, ocotea oil, patchouli oil, peppermint oil, perilla oil, petitgrain oil, pine oil, rose roil, rosemary oil, camphor oil, ho leaf oil, clary sage oil, sandalwood oil, spearmint oil, spike lavender oil, star anise oil, thyme oil, tonka bean tincture, turpentine oil, vanilla bean tincture, vetiver oil, bergamot oil, ylang ylang oil, grapefruit oil, yuzu (Citrus Junos Tanaka) oil, benzoin, balsam peru, balsam tolu, tuberose oil, musk tincture, castrium tincture, civet tincture, and ambergris tincture.

As mentioned above, the perfume oil represents between 0.1% to 60% w/w of the total weight of the entire liquid composition, and most preferably between 4 to 25%, or 5-20%, w/w of the total weight of the entire liquid composition.

In certain embodiments, the oil phase comprises at least 60% w/w fragrance ingredients, more preferably at least 90% w/w of fragrance or perfuming ingredients. In certain embodiments, the fragrance comprises one or more suitable solvents in quantity of up to 40% w/w of the oil phase, but, in certain embodiments, less than 10% w/w. As examples, suitable solvents include polar or non-polar low molecular weight solvents such as isoparaffins, hydrocarbons, silicon oils, glycols, glycol ethers, glycol ether esters, alcohols, or ketones.

The liquid composition of the invention also contains a fragrance vehicle, where the fragrance vehicle is miscible, partially miscible, or at least dispersible in both perfuming oil phase and water phase. The fragrance vehicle includes a single solvent or blend of solvents with a broad range of volatilities and polarities selected from the class of linear, branched, cyclic, or aromatic mono-, di- or poly-glycol-ethers or any combination thereof.

Non-limiting examples of suitable solvents from the above-mentioned classes are as follows: dihydric alcohol alkyl ethers, such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylehxyl ether, ethylene glycol isoamyl ether, ethylene glycol benzyl ether, ethylene glycol isopropyl ether, ethylene glycol: dimethyl ether, ethylene, glycol diethyl ether, and ethylene glycol dibutyl ether; dihydric alcohol alkyl ethers, such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether; dihydric alcohol ether esters, such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate; glycerol monoalkyl ethers, such as chimyl alcohol, selachyl alcohol, and butyl alcohol; POP butyl ether, POP-POE butyl ether, tripolyoxypropylene glycerol ether, POP glycerol ether, POP glycerol ether phosphate, and POP.POE pentaerythritol ether.

The above-mentioned fragrance vehicle compounds, which by their nature are solvents, have been found to enhance the solubility of otherwise less-soluble or immiscible organic compounds in water. The fragrance vehicle component allows water solubilization of a high level of fragrance oil with an low amount of solubilizing agent, whenever this is needed, compared with formulations containing the same amount of the same perfume, while the clarity and stability of the formulation are excellent, as is the release of the fragrance from the air-freshener.

In particular, the fragrance vehicle may be advantageously selected from mono-, di-, or poly-glycol ethers. In certain embodiments, the fragrance vehicle comprises 2-(2-butoxy-ethoxy)ethanol or (2-methoxy-methoxyethoxy)propanol or mixtures thereof.

According to particular embodiments of the invention, the amount of fragrance vehicle is between 10% to 30% by weight of the entire composition. It will be appreciated that the amount of fragrance vehicle needed to obtain a stable, clear, low viscosity composition having improved air-freshener performance depends on the specific nature of the perfume oil, the level of the perfume oil, the amount of solubilizing agent and the composition of the solubilizing agent. One of ordinary skill in the art will be able to determine an appropriate amount of fragrance vehicle using no more than routine experimentation in view of the disclosure herein.

As discussed herein, the liquid composition of the invention also includes a solubilizing agent (e.g., an amphiphilic solubilizing agent) that includes one or more anionic, cationic or amphoteric surfactants or a combination thereof.

Suitable solubilizing agents are selected from the group consisting of:

A. anionic surfactants, such as soap bases, sodium laurate, and sodium palmitate; higher alkyl sulfuric ester salts, such as sodium laurylsulfate and potassium laurylsulfate; alkyl ether sulfuric ester salts, such as triethanolamine POE laurylsulfate and sodium POE laurylsulfate; N-acylsarcosinic acids, such as sodium lauroylsarconinate, higher fatty acid amidosulfonates, such as sodium N-myristoyl-N-methyltaurine, sodium palm oil fatty acid methyltauride, and sodium laurylmethyltauride; phosphoric ester salts, such as sodium POE oleyl ether phosphate and POE stearyl ether phosphate; sulfosuccinates, such as sodium di-2-ethylhexylsulfosuccinate, and sodium lauryl polypropylene glycol sulfosuccinate; alkylbenzenesulfonates, such as sodium linear dodecylbenzenesulfonate, triethanolamine dodecylbenzenesulfonate, and linear dodecylbenzenesulfonic acid; N-acylglutamates, such as monosodium N-lauroylglutamate, disodium N-stearoylglutamate, monosodium N-myristoyl-L-glutamate; higher fatty acid ester sulfuric ester salts, such as sodium hydrogenated coconut oil fatty acid glycerol sulfate; sulfated oils, such as Turkey red oil; POE alkyl ether carboxylic acids, POE alkyl allyl, ether carboxylates, α-olefinsulfonates, higher fatty acid ester sulfonates, secondary alcohol sulfuric ester salts, higher fatty acid alkylolamide sulfuric ester salts, sodium lauroyl monoethanolamide succinate, ditriethanolamine N-palmitoylaspartate, and sodium casein;

B. cationic surfactants, such as stearyltrimethylammonium chloride and lauryltrimethylammonium chloride; dialkyldimethylammonium salts, such as distearyldimethylammonium chloride, alkylpyridinium salts, such as poly-N,N'-dimethyl-3,5-methylenepiperidinium chloride; alkyl quaternary ammonium salts, alkyldimethylbenzylammonium salts, alkylisoquinolinium salts, dialkylmorpholinium salts, POE alkylamines, alkylamine salts, polyamine fatty acid derivatives, amyl alcohol fatty acid derivatives, benzalkonium chloride, and benzethonium chloride.

C. amphoteric surfactants, such as sodium 2-undecyl-N,N,N-(hydroxyethylcarboxymethyl)-2-imidazoline and disodium 2-cocoyl-2-imidazolinium hydroxide-1-carboxyethyloxy; 2-heptadecyl-N-carboxymethyl-N-hydroxyethylimidazolinium betaine, alkyl betaines, amide betaines, and sulfobetaines.

D. lipophilic nonionic surfactants, such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate; glycerol or polyglycerol fatty acids esters, such as glycerol mono-cotton seed oil fatty acid ester, glycerol monoerucate, glycerol sesquioleate, glycerol monostearate, glycerol α,α'-oleate pyroglutamate, and glycerol monostearate maleate; propylene glycol fatty acid esters, such as propylene glycol monostearate; hydrogenated castor oil derivatives, and glycerol alkyl ethers.

E. hydrophilic nonionic surfactants, such as POE sorbitan monooleate, POE sorbitan monostearate, POE sorbitan monooleate, and POE sorbitan tetraoleate; POE sorbitol fatty acid esters, such as POE sorbitol monolaurate, POE sorbitol monooleate, POE sorbitol pentaoleate, and POE sorbitol monostearate; POE glycerol fatty acid esters, such as POE glycerol monostearate, POE glycerol monoisostearate, and POE glycerol triisostearate; POE fatty acid esters, such as POE monooleate, POE distearate, POE monodioleate, and ethylene glycol distearate; POE alkyl ethers, such as POE lauryl ether, POE oleyl ether, POE stearyl ether, POE behenyl ether, POE-2-octyldodecyl ether, and POE-cholestanol ether; POE alkyl phenyl ethers, such as POE octyl phenyl ether, POE nonyl phenyl ether, and POE dinonylphenyl ether; Pluronic type surfactants, such as Pluronic; POE.POP alkyl ethers, such as POE.POP cetyl ether, POE.POP 2-decyltetradecyl ether, POE.POP monobutyl ether, POE.POP hydrogenated lanolin, and POE-POP glycerol ether; tetraPOE.tetraPOP ethylenediamine condensates, such as Tetronic; POE castor oil or hydrogenated castor oil derivatives, such as POE castor oil, POE hydrogenated castor oil, POE hydrogenated castor oil monoisostearate, POE hydrogenated castor oil triisostearate, POE hydrogenated castor oil monopyroglutamate monoisostearate, and POE hydrogenated castor oil maleate; POE beeswax lanolin derivatives, such as POE sorbitol beeswax; alkanolamides, such as coconut oil fatty acid diethanolamide, lauric acid monoethanolamide, and fatty acid isopropanolamides; POE propylene glycol fatty acid esters, POE alkylamines, POE fatty acid amides, sucrose fatty acid esters, POE nonylphenyl formaldehyde condensates, alkylethoxydimethylamine oxides, and trioleyl phosphate; and F. mixtures thereof.

In certain embodiments, the solubilizing agent comprises one or more anionic surfactants.

In all embodiments of the invention the level of solubilizing agent is very low, e.g., the weight ratio of solubilizing gent, such as surfactant, to fragrance oil is below 1:1, preferably below 0.3:1.

The liquid air-freshener composition of the invention also includes water, which is preferably distilled or de-ionized water.

In certain embodiments, the air freshener composition further comprises one or more additional additives, such as antioxidants, dyes, UV stabilizers, buffer agents, pH controlling mixtures, malodor control agents, and antibacterial agents, sa are known in the art.

In certain embodiments, the composition has 18% or less volatile organic compounds (VOC) as defined by CARB. In certain embodiments, a volatile organic compound is any organic compound whose boiling point is in the range from (50° C. to 100° C.) to (240° C. to 260° C.), corresponding to having saturation vapour pressures at 25° C. greater than 102 kPa.

In another aspect, the invention provides an air freshener system, comprising:
(i) a container;
(ii) a composition of the invention as described herein:
(iii) a diffuser for diffusing the liquid composition into surrounding air or
(iv) a nozzle for spraying the liquid composition into surrounding air.

The container can be made of any suitable material, e.g., glass, plastic, and the like, and in certain embodiments, the container can be sealed. In certain embodiments, the diffuser comprises one or more wicks, reeds, or other natural or synthetic porous diffusing devices. In certain embodiments, the air freshener further comprises removable means for preventing diffusion of the liquid composition into surrounding air (e.g., a lid, cap, or other removable closure for the container). In certain embodiments, the air freshener releases fragrance for at least 2 weeks after opening or activation.

In another aspect, the invention provides a consumer article comprising a liquid composition as described herein. A consumer article includes, e.g., a scented article, an air freshener device, a spray (e.g., an aerosol or pump spray canister), and the like.

In yet another aspect, the invention provides a method of providing a fragrance to ambient air, the method comprising diffusing or spraying a liquid air freshener composition according to the invention into the ambient air.

Thus, in certain embodiments, the invention provides:
(I) a liquid air freshener device for perfuming, freshening, or malodor cleaning, neutralizing or counteracting the surroundings that comprises:
A. a vessel or container carrying a liquid composition that contains:
  i. 0.1 to 60% (e.g., 0.1 to 40%) w/w oil-phase (also referred to herein as "perfume");
  ii. at least 10% (e.g., at least 30%) w/w water-phase;
  iii. between 10% to 30% low VOC or substantially completely non-VOC fragrance vehicle, which contains one or more mono-, di- or poly-glycol ethers, such as 2-(2-butoxy-ethoxy)ethanol or (2-methoxymethoxyethoxy) propanol or mixtures thereof;
  iv. a low level of amphiphilic solubilizing agents such as surfactants (e.g., the weight ratio of surfactant to fragrance oil is below 1:1, preferably below 0.3:1);
  weight percentages being relative to the total weight of liquid composition unless otherwise stated;
B. an emanating surface capable of providing for diffusion of the mentioned liquid composition;
C. means for carrying the said liquid composition from the container vessel to the emanating surface or device; and
D. optionally, removable means, usable by a user, for preventing diffusion of the liquid composition prior to the activation of the air freshener device.

The means for carrying the said liquid composition from the container vessel to the emanating surface or device can be any element known in the art for carrying or transporting a liquid composition, e.g., a tube, channel, pipe, wick, reed, and the like.

The removable means for preventing diffusion of the liquid composition prior to the activation of the air freshener device can be a removable cap, lid, closure, valve, or any other element or structure that can prevent diffusion of the liquid composition prior to the activation of the air freshener device, but can be opened or removed to permit diffusion of the liquid composition upon activation of the device.

Examples of devices The air include those devices set forth in U.S. Pat. No. 4,663,081, issued on May 5, 1987, which is incorporated by reference herein.

(II) An air freshener device according to (I), wherein component C is a wick, reeds or any natural or synthetic porous diffuser;

(III) An air freshener device according to (I), wherein component C is a nozzle spray with actuator;

(IV) An air freshener device according to (II) and (III), wherein the weight ratio between the solubilizing agent and oil-phase is less than 1.

(V) An air freshener device for perfuming or refreshing the surroundings that comprises:

E. a vessel or container carrying a liquid composition that contains:
  v. 0.1 to 40% w/w oil-phase (also referred to herein as "perfume");
  vi. at least 30% w/w water-phase;
  vii. between 10% to 30% low VOC or completely non-VOC fragrance vehicle, which contains one or more mono-, di- or poly-glycol ethers, specifically 2-(2-butoxy-ethoxy)ethanol or (2-methoxy-methoxy-lethoxy) propanol or established mixtures of those;
  viii. low level of amphiphilic solubilizing agents such as surfactants.

F. an emanating surface capable of providing for diffusion of said liquid composition;

G. means for carrying the said liquid composition from the container vessel to the emanating surface or device; and H. optionally, removable means used by user for preventing diffusion of the liquid composition prior to the activation of the air freshener device;

I. a nozzle capable of spraying of said liquid composition;

(VI) An air freshener device according to (V), wherein component L is a wick, reeds or any natural or synthetic porous diffuser;

(VII) An air freshener device according to (V), wherein component L is a nozzle spray with actuator;

(VIII) An air freshener device according to (I) or (V), wherein the solubilizing agent is selected from group consisting of:

A. anionic surfactants, such as soap bases, sodium laurate, and sodium palmitate; higher alkyl sulfuric ester salts, such as sodium laurylsulfate and potassium laurylsulfate; alkyl ether sulfuric ester salts, such as triethanolamine POE laurylsulfate and sodium POE laurylsulfate; N-acylsarcosinic acids, such as sodium lauroylsarconinate, higher fatty acid amidosulfonates, such as sodium N-myristoyl-N-methyltaurine, sodium palm oil fatty acid methyltauride, and sodium laurylmethyltauride; phosphoric ester salts, such as sodium POE oleyl ether phosphate and POE stearyl ether phosphate; sulfosuccinates, such as sodium di-2-ethylhexylsulfosuccinate, and sodium lauryl polypropylene glycol sulfosuccinate; alkylbenzenesulfonates, such as sodium linear dodecylbenzenesulfonate, triethanolamine dodecylbenzenesulfonate, and linear dodecylbenzenesulfonic acid; N-acylglutamates, such as monosodium N-lauroylglutamate, disodium N-stearoylglutamate, monosodium N-myristoyl-L-glutamate; higher fatty acid ester sulfuric ester salts, such as sodium hydrogenated coconut oil fatty acid glycerol sulfate; sulfated oils, such as Turkey red oil; POE alkyl ether carboxylic acids, POE alkyl allyl, ether carboxylates, α-olefinsulfonates, higher fatty acid ester sulfonates, secondary alcohol sulfuric ester salts, higher fatty acid alkylolamide sulfuric ester salts, sodium lauroyl monoethanolamide succinate, ditriethanolamine N-palmitoylaspartate, and sodium casein;

B. cationic surfactants, such as stearyltrimethylammonium chloride and lauryltrimethylammonium chloride; dialkyldimethylammonium salts, such as distearyldimethylammonium chloride, alkylpyridinium salts, such as poly-N,N'-dimethyl-3,5-methylenepiperidinium chloride; alkyl quaternary ammonium salts, alkyldimethylbenzylammonium salts, alkylisoquinolinium salts, dialkylmorpholinium salts, POE alkylamines, alkylamine salts, polyamine fatty acid derivatives, amyl alcohol fatty acid derivatives, benzalkonium chloride, and benzethonium chloride.

C. amphoteric surfactants, such as sodium 2-undecyl-N,N,N-(hydroxyethylcarboxymethyl)-2-imidazoline and disodium 2-cocoyl-2-imidazolinium hydroxide-1-carboxyethyloxy; 2-heptadecyl-N-carboxymethyl-N-hydroxyethylimidazolinium betaine, alkyl betaines, amide betaines, and sulfobetaines.

D. lipophilic nonionic surfactants, such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate; glycerol or polyglycerol fatty acids esters, such as glycerol mono-cotton seed oil fatty acid ester, glycerol monoerucate, glycerol sesquioleate, glycerol monostearate, glycerol α,α'-oleate pyroglutamate, and glycerol monostearate maleate; propylene glycol fatty acid esters, such as propylene glycol monostearate; hydrogenated castor oil derivatives, and glycerol alkyl ethers.

E. hydrophilic nonionic surfactants, such as POE sorbitan monooleate, POE sorbitan monostearate, POE sorbitan monooleate, and POE sorbitan tetraoleate; POE sorbitol fatty acid esters, such as POE sorbitol monolaurate, POE sorbitol monooleate, POE sorbitol pentaoleate, and POE sorbitol monostearate; POE glycerol fatty acid esters, such as POE glycerol monostearate, POE glycerol monoisostearate, and POE glycerol triisostearate; POE fatty acid esters, such as POE monooleate, POE distearate, POE monodioleate, and ethylene glycol distearate; POE alkyl ethers, such as POE lauryl ether, POE oleyl ether, POE stearyl ether, POE behenyl ether, POE-2-octyldodecyl ether, and POE-cholestanol ether; POE alkyl phenyl ethers, such as POE octyl phenyl ether, POE nonyl phenyl ether, and POE dinonylphenyl ether; Pluronic type surfactants, such as Pluronic; POE.POP alkyl ethers, such as POE.POP cetyl ether, POE.POP 2-decyltetradecyl ether, POE.POP monobutyl ether, POE.POP hydrogenated lanolin, and POE-POP glycerol ether; tetraPOE.tetraPOP ethylenediamine condensates, such as Tetronic; POE castor oil or hydrogenated castor oil derivatives, such as POE castor oil, POE hydrogenated castor oil, POE hydrogenated castor oil monoisostearate, POE hydrogenated castor oil triisostearate, POE hydrogenated castor oil monopyroglutamate monoisostearate, and POE hydrogenated castor oil maleate; POE beeswax lanolin derivatives, such as POE sorbitol beeswax; alkanolamides, such as coconut oil fatty acid diethanolamide, lauric acid monoethanolamide, and fatty acid isopropanolamides; POE propylene glycol fatty acid esters, POE alkylamines, POE fatty acid amides, sucrose fatty acid esters, POE nonylphenyl formaldehyde condensates, alkylethoxydimethylamine oxides, and trioleyl phosphate; and F. mixtures thereof.

(IX) Use of a liquid composition according to (I) and (V) to confer, enhance, modify or freshen the odor and ambient quality of a room, an open space, a closet or other closed space.

The invention further provides a method of using the above-mentioned liquid composition, e.g., in devices that allow the release of the liquid composition into the surrounding air through wicks, reeds, or any natural or synthetic porous materials, or by spraying thorough a nozzle, while the said releasing devices offer unusual product longevity and outstanding fragrance intensity.

As described herein, in general, the liquid compositions of the invention include at least four parts: part A, the perfume or oil phase, which mainly contains fragrance ingredients; part B, the fragrance vehicle, which is a solvent or blend of solvents with a broad range of volatilities and polarities selected from the class of linear, branched, cyclic, or aromatic mono-, di- or glycol-ethers or any combination thereof; part C, the solubilizing agent, which is a surfactant, such as ionic or non-ionic surfactants or a combination of thereof; and part D, the water phase, which is mainly water.

In a preferred embodiment, the liquid air freshener contains:
ix. to 40% w/w oil-phase (also referred to herein as "perfume");
x. between 10% to 30% low VOC or substantially completely non-VOC fragrance vehicle, which contains one or more mono-, di- or poly-glycol ethers, specifically 2-(2-butoxy-ethoxy)ethanol or (2-methoxy-methoxy-lethoxy) propanol or established mixtures of those;
xi. low level of amphiphilic solubilizing agent, such as surfactants, at a weight ratio surfactant versus fragrance less than 1;
xii. at least 30% w/w water.

As used herein, a low VOC or substantially completely non-VOC fragrance vehicle is a fragrance vehicle having a low level of VOCs (e.g., less than 50%, less than 20%, less than 10%, less than 5%, less than 1%) or substantially no VOCs.

Without wishing to be bound by any particular theory, it is believed that a very low interfacial tension between perfume and external water phase is achieved through an interfacial synergistic mechanism that allows control of the amount of solubilizing agent. A very low interfacial tension between perfume and external water-phase can be achieved by bridging the lipophilic character of the perfume with the external water-phase, which can be achieved by simultaneously matching the HLB value of the solubilizing agent with the solubilizing parameter of the fragrance vehicle and with the overall hydrophilic lipophilic characteristics of the fragrance ingredients versus the external water-phase. Without wishing to be bound by any particular theory, it is believed that, once established, the interfacial synergistic mechanism can allow the fragrance solubilisation into a high water content environment with a minimum amount of solubilizer. This feature permits excellent robustness to solubilise a wide variety of fragrance compositions regardless of hydrophilic-lipophilic characteristics or its ClogP value, and permits the formulation of air freshener products that can be released into the surroundings through wicks, reeds, natural or synthetic porous materials, or the like.

The fragrance vehicle composition includes a suitable solvents from the following non-limiting classes of linear, branched, cyclic, or aromatic mono-, di- or poly-glycol-ethers: dihydric alcohol alkyl ethers, such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol: dimethyl ether, ethylene, glycol diethyl ether, and ethylene glycol dibutyl ether; dihydric alcohol alkyl ethers, such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether; dihydric alcohol ether esters, such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate; glycerol monoalkyl ethers, such as chimyl alcohol, selachyl alcohol, and butyl alcohol; POP butyl ether, POP-POE butyl ether, tripolyoxypropylene glycerol ether, POP glycerol ether, POP glycerol ether phosphate, and POP.POE pentaerythritol ether.

The solubilizing agent can be ionic or non-ionic, such as surfactants, or mixture thereof. The ionic surfactants can be anionic, cationic or amphoteric molecules described herein or as known to the skilled artisan.

Non-limiting examples of suitable anionic surfactants include fatty acid soaps, such as soap bases, sodium laurate, and sodium palmitate; higher alkyl sulfuric ester salts, such as sodium laurylsulfate and potassium laurylsulfate; alkyl ether sulfuric ester salts, such as triethanolamine POE laurylsulfate and sodium POE laurylsulfate; N-acylsarcosinic acids, such as sodium lauroylsarconinate, higher fatty acid amidosulfonates, such as sodium N-myristoyl-N-methyltaurine, sodium palm oil fatty acid methyltauride, and sodium laurylmethyltauride; phosphoric ester salts, such as sodium POE oleyl ether phosphate and POE stearyl ether phosphate; sulfosuccinates, such as sodium di-2-ethylhexylsulfosuccinate, sodium POE monolauroylmonoethanolamide sulfosuccinate, and sodium lauryl polypropylene glycol sulfosuccinate; alkylbenzenesulfonates, such as sodium linear dodecylbenzenesulfonate, triethanolamine linear dodecylbenzenesulfonate, and linear dodecylbenzenesulfonic acid; N-acylglutamates, such as monosodium N-lauroylglutamate, disodium N-stearoylglutamate, monosodium N-myristoyl-L-glutamate; higher fatty acid ester sulfuric ester salts, such as sodium hydrogenated coconut oil fatty acid glycerol sulfate; sulfated oils, such as Turkey red oil; POE alkyl ether carboxylic acids, POE alkyl allyl, ether carboxylates, α-olefinsulfonates, higher fatty acid ester sulfonates, secondary alcohol sulfuric ester salts, higher fatty acid alkylolamide sulfuric ester salts, sodium lauroyl monoethanolamide succinate, ditriethanolamine N-palmitoylaspartate, and sodium casein.

Non-limiting examples of suitable cationic surfactants include alkyltrimethylammonium salts, such as stearyltrimethylammonium chloride and lauryltrimethylammonium chloride; dialkyldimethylammonium salts, such as distearyldimethylammonium chloride, alkylpyridinium salts, such as poly-N,N'-dimethyl-3,5-methylenepiperidinium chloride; alkyl quaternary ammonium salts, alkyldimethylbenzylammonium salts, alkylisoquinolinium salts, dialkylmorpholinium salts, POE alkylamines, alkylamine salts, polyamine fatty acid derivatives, amyl alcohol fatty acid derivatives, benzalkonium chloride, and benzethonium chloride.

Non-limiting examples of suitable amphoteric surfactants include imidazoline surfactants, such as sodium 2-undecyl-N,N,N-(hydroxyethylcarboxymethyl)-2-imidazoline and disodium 2-cocoyl-2-imidazolinium hydroxide-1-carboxyethyloxy; and betaines, such as 2-heptadecyl-N-carboxymethyl-N-hydroxyethylimidazolinium betaine, alkyl betaines, amide betaines, and sulfobetaines.

Non-limiting examples of suitable lipophilic nonionic surfactants include sorbitan fatty acid esters, such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate; glycerol or polyglycerol fatty acids esters, such as glycerol mono-cotton seed oil fatty acid ester, glycerol monoerucate, glycerol sesquioleate, glycerol monostearate, glycerol $\alpha,\alpha'$-oleate pyroglutamate, and glycerol monostearate maleate; propylene glycol fatty acid esters, such as propylene glycol monostearate; hydrogenated castor oil derivatives, and glycerol alkyl ethers.

Non-limiting examples of suitable hydrophilic nonionic surfactants include POE sorbitan fatty acid esters, such as POE sorbitan monooleate, POE sorbitan monostearate, POE sorbitan monooleate, and POE sorbitan tetraoleate; POE sorbitol fatty acid esters, such as POE sorbitol monolaurate, POE sorbitol monooleate, POE sorbitol pentaoleate, and POE sorbitol monostearate; POE glycerol fatty acid esters, such as POE glycerol monostearate, POE glycerol monoisostearate, and POE glycerol triisostearate; POE fatty acid esters, such as POE monooleate, POE distearate, POE monodioleate, and ethylene glycol distearate; POE alkyl ethers, such as POE lauryl ether, POE oleyl ether, POE stearyl ether, POE behenyl ether, POE-2-octyldodecyl ether, and POE-cholestanol ether; POE alkyl phenyl ethers, such as POE octyl phenyl ether, POE nonyl phenyl ether, and POE dinonylphenyl ether; Pluronic type surfactants, such as Pluronic; POE.POP alkyl ethers, such as POE.POP cetyl ether, POE.POP 2-decyltetradecyl ether, POE.POP monobutyl ether, POE.POP hydrogenated lanolin, and POE-POP glycerol ether; tetraPOE.tetraPOP ethylenediamine condensates, such as Tetronic; POE castor oil or hydrogenated castor oil derivatives, such as POE castor oil, POE hydrogenated castor oil, POE hydrogenated castor oil monoisostearate, POE hydrogenated castor oil triisostearate, POE hydrogenated castor oil monopyroglutamate monoisostearate, and POE hydrogenated castor oil maleate; POE beeswax lanolin derivatives, such as POE sorbitol beeswax; alkanolamides, such as coconut oil fatty acid diethanolamide, lauric acid monoethanolamide, and fatty acid isopropanolamides; POE propylene glycol fatty acid esters, POE alkylamines, POE fatty acid amides, sucrose fatty acid esters, POE nonylphenyl formaldehyde condensates, alkylethoxydimethylamine oxides, and trioleyl phosphate.

The water, which represents at least 30% w/w of the entire composition, can also contain miscible or partial miscible hydrophilic ingredients such as antioxidants, UV stabilizers, buffer agents, pH controlling mixtures, malodour control and antibacterial agents.

The compositions and methods of the invention can provide more environmentally safe, water-based, low- or free-VOC air fresheners that can contain variable amounts of fragrances, while said air freshener composition is released into the surroundings either through a sustained release system based on wicks, reeds, natural or synthetic porous materials or the like, or through controlled release systems such as sprays or aerosols. In addition, there are fewer limitations regarding the fragrance formulation, while the releasing devices including a composition of the invention in preferred embodiments, offer excellent product stability, longevity, and outstanding fragrance performance, such as fragrance intensity, character, and diffusitivity into surroundings, due to enhanced fragrance solubilization into the water phase. If malodor control agents are used, the method may also provide a cover-up, reduction or complete neutralization in malodors.

Also, depending on the solubilizing system both the lower and the upper temperature limits of stability of the final product can be extended The following examples are intended to illustrate and not to limit the scope of the invention.

EXAMPLES

Examples 1-4

Exemplary Air Freshener Formulations

| Formula | #1 | #2 | #3 | #4 |
|---|---|---|---|---|
| Aerosol OT-75* | 1.0 | 4.0 | 5.3 | 2.5 |
| Methyl Carbitol** | 10.0 | 10.0 | 5.3 | 10.0 |
| Butyl Carbitol*** | 25.0 | 25.0 | 21.0 | 25.0 |
| Orange Concentrate**** | — | 10.0 | 52.6 | — |
| Peach Apple Crisp**** | 5.0 | — | — | 10.0 |
| Water | 59.0 | 51.0 | 15.8 | 52.5 |

*Aerosol OT-75 is sodium di-2-ethylhexylsulfosuccinate from Cytec, Inc.
**Methyl Carbitol is Propanol, (2-methoxy-methylethoxy) from Dow Chemical
***Butyl Carbitol is Ethanol, 2-(2-butoxy-ethoxy) from Dow Chemical
****Peach Apple Crisp, Orange Concentrate are fragrance concentrates available from Agilex Flavors and Fragrances
****Peach Apple Crisp fragrance formula:
Aldehyde C-14
Amyl Butyrate Normal
Caryophyllene Beta
Cinnamic Aldehyde
Cinnamon Leaf Ceylon
Clove Bud Oil Madagascar
Damascone Delta
Dimethyl Benzyl Carbinyl Butyrate
Ethylene Brassylate
Ethyl -2-Methyl Butyrate
Ethyl Vanillin
Fructone
Hexalon (Allyl Ionone)
Leaf Acetate (cis-3-Hexenyl Acetate)
Leaf Alcohol (cis-3-hexenol)
Leaf Aldehyde (trans-2-Hexenal)
Lemon Oil
Lime Oil Roses Type 5825
Verdox
****Orange Concentrate fragrance formula:
L-Borneol Crystals
Cassis Base 345B
Citronellol AJ
Cyclamal
Geraniol BJ
Grapefruit Terpenes
Cis-3-Hexenyl Butyrate
Ionone Beta
Lemon Oil Argentina
Linalool
Para Cymene
Petitgrain Oil
Triplal
Vertenex

Examples 5-8

Exemplary Air Freshener Formulations

| Formula | #5 | #6 | #7 | #8 |
|---|---|---|---|---|
| Aerosol OT-75* | 1.5 | 2.0 | 1.0 | 1.5 |
| Methyl Carbitol** | 10.0 | 10.0 | 10.0 | 10.0 |
| Butyl Carbitol*** | 20.0 | 30.0 | 30.0 | 30.0 |
| Peach Apple Crisp**** | 5.0 | — | 15.0 | 20.0 |
| Orange Concentrate**** | — | 15.0 | | |
| Water | 63.5 | 43.0 | 44.0 | 38.5 |

*Aerosol OT-75 is sodium di-2-ethylhexylsulfosuccinate from Cytec, Inc.
**Methyl Carbitol is Propanol, (2-methoxy-methylethoxy) from Dow Chemical
***Butyl Carbitol is Ethanol, 2-(2-butoxy-ethoxy) from Dow Chemical
****Peach Apple Crisp and Orange Concentrate are fragrance concentrates available from Agilex Flavors and Fragrances (see Examples 1-4).

Examples 9-12

Exemplary Air Freshener Formulations

| Formula | Example #9 | Example #10 | Example #11 | Example #12 |
|---|---|---|---|---|
| SLES 30%* | — | — | 3.0 | — |
| Aerosol OT-75** | 1.5 | 2.5 | — | 1.0 |
| Methyl Carbitol*** | 4.0 | 4.0 | 1.0 | 1.0 |
| Butyl Carbitol**** | 25.0 | 22.0 | 20.0 | 24.0 |
| Orange Concentrate***** | 5.0 | 10.0 | — | — |
| Peach Apple Crisp***** | — | — | 5.0 | 5.0 |
| Water | 64.5 | 61.5 | 71.0 | 69.0 |

*SLES 30% is sodium lauryl ether sulfate from Pilot Chemical Company
**Aerosol OT-75 is sodium di-2-ethylhexylsulfosuccinate from Cytec, Inc.
***Methyl Carbitol is Propanol, (2-methoxy-methylethoxy) from Dow Chemical
**** Butyl Carbitol is Ethanol, 2-(2-butoxy-ethoxy) from Dow Chemical
*****Peach Apple Crisp and Orange Concentrate are fragrance concentrates available from Agilex Flavors and Fragrances (see Examples 1-4).

Examples 13-16

Exemplary Air Freshener Formulations

| Formula | Example #13 | Example #14 | Example #15 | Example #16 |
|---|---|---|---|---|
| SLES 30%* | — | — | — | 5.0 |
| Aerosol OT-75** | 2.5 | 2.0 | 3.0 | — |
| Methyl Carbitol*** | 1.0 | 1.0 | — | 1.0 |
| Butyl Carbitol**** | 28.0 | 28.5 | 25.0 | 28.0 |
| Orange Concentrate***** | — | 15.0 | 20.0 | — |
| Peach Apple Crisp***** | 15.0 | — | — | 15.0 |
| Water | 53.5 | 53.5 | 52.0 | 51.0 |

*SLES 30% is sodium lauryl ether sulfate from Pilot Chemical Company
**Aerosol OT-75 is sodium di-2-ethylhexylsulfosuccinate from Cytec, Inc.
***Methyl Carbitol is Propanol, (2-methoxy-methylethoxy) from Dow Chemical
****Butyl Carbitol is Ethanol, 2-(2-butoxy-ethoxy) from Dow Chemical
*****Peach Apple Crisp and Orange Concentrate are fragrance concentrates available from Agilex Flavors and Fragrances (see Examples 1-4).

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or sub combination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A liquid air freshener composition, the composition comprising:
   (a) 0.1% to 40% by weight of an oil phase comprising a fragrance;
   (b) at least 50% by weight of water;
   (c) a fragrance vehicle comprising at least one mono-, di-, or polyglycol ether; and
   (d) an amphiphilic solubilizing agent, wherein the weight ratio of the amphiphilic solubilizing agent to the oil phase comprising a fragrance is less than 1:1, wherein the weight percentages are based on the total weight of the liquid air freshener composition.

2. A liquid air freshener composition of claim 1, wherein the composition comprises 0.5% to 40% by weight of an oil phase comprising a fragrance.

3. A liquid air freshener composition of claim 1, wherein the composition comprises:
   (a) 0.1 to 40% by weight of an oil phase comprising a fragrance;
   (b) an amphiphilic oil solubilizing agent comprising one or more ionic, non-ionic, cationic or amphoteric surfactants, or a mixture thereof; and
   (c) a low VOC fragrance vehicle comprising at least one linear, branched, cyclic, or aromatic mono-, di- or poly-glycol-ether.

4. The air freshener composition of claim 1, wherein the composition is a clear isotropic composition.

5. The air freshener composition of claim 1, wherein the composition is a microemulsion or nanoemulsion.

6. The air freshener composition claim 1, wherein the composition is a solution.

7. The air freshener composition of claim 6, wherein the solution is a micellar solution.

8. The air freshener composition of claim 1, wherein the fragrance comprises one or more fragrance components selected from the group consisting of ketones, aldehydes, esters, alcohols, ethers, terpenes, natural essential oils, and synthetic musk.

9. The air freshener composition of claim 1, wherein the amphiphilic solubilizing agent comprises one or more surfactants or hydrotropic molecules, or a combination thereof.

10. The air freshener composition of claim 9, wherein the amphiphilic solubilizing agent comprises one or more ionic, non-ionic, anionic, cationic or amphoteric surfactants.

11. The air freshener composition of claim 1, wherein the fragrance vehicle comprises 2-(2-butoxy-ethoxy)ethanol or (2-methoxy-methylethoxy)propanol.

12. The air freshener composition of claim 1, wherein the fragrance vehicle is a low VOC fragrance vehicle.

13. The air freshener composition of claim 1, wherein the fragrance vehicle comprises a material selected from the group consisting of dihydric alcohol alkyl ethers; dihydric alcohol alkyl ethers; dihydric alcohol ether esters; glycerol monoalkyl ethers; POP butyl ether, POP-POE butyl ether, tripolyoxypropylene glycerol ether, POP glycerol ether, POP glycerol ether phosphate, and POP.POE pentaerythritol ether; or a mixture thereof.

14. The air freshener composition of claim 1, wherein the composition comprises between 10% to 30% fragrance vehicle by weight.

15. The air freshener composition of claim 1, wherein the liquid composition comprises a solubilizing agent at a weight ratio between 0.1:1 to 1:1 relative to the weight of the oil phase.

16. An air freshener system, comprising:
 (i) a container;
 (ii) an air freshener composition of claim 1; and
 (iii) a diffuser for diffusing the liquid composition into surrounding air.

17. The air freshener system of claim 16, wherein the diffuser is a natural or synthetic porous material that allows the diffusion of the claimed composition.

18. The air freshener system of claim 16, wherein the diffuser comprises one or more wicks, reeds, or natural or synthetic porous diffusers.

19. The air freshener system of claim 16, wherein the air freshener system further comprises removable means for preventing diffusion of the liquid composition into surrounding air.

20. The air freshener system of claim 16, wherein the air freshener system releases fragrance for at least 2 weeks after opening.

21. A method of providing a fragrance to ambient air, the method comprising diffusing a liquid air freshener composition with the device according to claim 16 into the ambient air.

22. A method for perfuming, refreshing, disinfecting or cleaning ambient air, the method comprising diffusing a liquid air freshener composition with the device according to claim 16 into the ambient air.

23. An air freshener system, comprising:
 (i) a container;
 (ii) an air freshener composition of claim 1; and
 (iii) means for carrying the liquid composition from the container to an emanating nozzle for spraying the said composition; and
 (iv) an actuator device for controlling the spraying of the said liquid composition from the container into the surrounding air environment.

24. A consumer article comprising a composition claim 1.

* * * * *